United States Patent
Chaki et al.

(10) Patent No.: US 10,829,426 B2
(45) Date of Patent: *Nov. 10, 2020

(54) COMPOSITION CONTAINING HYDROFLUOROOLEFIN COMPOUND

(71) Applicant: DAIKIN INDUSTRIES, LTD., Osaka (JP)

(72) Inventors: Takehiro Chaki, Osaka (JP); Daisuke Karube, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/535,487

(22) Filed: Aug. 8, 2019

(65) Prior Publication Data

US 2020/0031745 A1 Jan. 30, 2020

Related U.S. Application Data

(63) Continuation of application No. 15/559,545, filed as application No. PCT/JP2016/060600 on Mar. 31, 2016, now Pat. No. 10,472,309.

(30) Foreign Application Priority Data

Mar. 31, 2015 (JP) .................................. 2015-072739

(51) Int. Cl.
| | |
|---|---|
| C07C 21/18 | (2006.01) |
| C07C 21/04 | (2006.01) |
| C07C 21/06 | (2006.01) |
| C07C 19/08 | (2006.01) |
| C07C 19/10 | (2006.01) |
| C09K 3/30 | (2006.01) |
| C09K 5/04 | (2006.01) |
| C07C 19/04 | (2006.01) |
| C07C 21/073 | (2006.01) |

(52) U.S. Cl.
CPC .............. *C07C 21/18* (2013.01); *C07C 19/04* (2013.01); *C07C 19/08* (2013.01); *C07C 19/10* (2013.01); *C07C 21/04* (2013.01); *C07C 21/06* (2013.01); *C07C 21/073* (2013.01); *C09K 3/30* (2013.01); *C09K 5/04* (2013.01); *C09K 5/044* (2013.01); *C09K 2205/126* (2013.01)

(58) Field of Classification Search
None
See application file for complete search history.

(56) References Cited

U.S. PATENT DOCUMENTS

| | | | |
|---|---|---|---|
| 7,077,960 | B2 | 7/2006 | Balthasat |
| 8,419,968 | B2 | 4/2013 | Carr |
| 8,975,454 | B2 | 3/2015 | Merkel |
| 2006/0185972 | A1 | 8/2006 | Balthasart et al. |
| 2007/0112227 | A1 | 5/2007 | Mukhopadhyay et al. |
| 2011/0031436 | A1 | 2/2011 | Mahler |
| 2011/0160497 | A1 | 6/2011 | Deur-Bert et al. |
| 2012/0203037 | A1 | 8/2012 | Sharratt et al. |
| 2013/0152626 | A1 | 6/2013 | Feng |
| 2014/0275655 | A1 | 9/2014 | Wang |
| 2015/0008357 | A1 | 1/2015 | Furuta |
| 2015/0322317 | A1 | 11/2015 | Collier et al. |
| 2015/0353799 | A1 | 12/2015 | Deur-Bert et al. |
| 2016/0340565 | A1 | 11/2016 | Tasaka |
| 2016/0355453 | A1* | 12/2016 | Ohkubo ............... B01J 23/6522 |

FOREIGN PATENT DOCUMENTS

| | | |
|---|---|---|
| CN | 101351430 | 1/2009 |
| JP | 2011-520017 | 7/2011 |
| JP | 2013-529703 | 7/2013 |
| JP | 2015-500362 | 1/2015 |
| JP | 2015-502450 | 1/2015 |
| JP | 2015-120669 | 7/2015 |
| WO | 2007/056127 | 5/2007 |
| WO | 2009/137658 | 11/2009 |
| WO | 2011/163117 | 12/2011 |
| WO | 2013/082963 | 6/2013 |
| WO | 2013/096005 | 6/2013 |
| WO | 2013/154059 | 10/2013 |
| WO | 2014/102478 | 7/2014 |
| WO | 2014/102479 | 7/2014 |
| WO | 2015/125874 | 8/2015 |

OTHER PUBLICATIONS

Extended European Search Report dated Jan. 23, 2019 in corresponding European patent application No. 16773085.2.
Partial Supplementary European Search Report dated Sep. 20, 2018 in corresponding European patent application No. 16773085.2.
International Search Report dated Jul. 5, 2016 in International (PCT) Application No. PCT/JP2016/060600.
Deur-Bert, D. et al. Publication No. WO2014/102478, Published Jul. 3, 2014, pp. 1-4; English translation (Year: 2014).

* cited by examiner

*Primary Examiner* — Medhanit W Bahta
(74) *Attorney, Agent, or Firm* — Wenderoth, Lind & Ponack, L.L.P.

(57) ABSTRACT

The present invention provides a composition comprising an HFO compound, the composition having excellent stability with decomposition and oxidation of the HFO compound being inhibited, the composition having improved refrigerating capacity when used as a heat transfer medium, compared with the case in which an HFO compound is used alone. More specifically, the present invention provides a composition comprising at least one HFO compound selected from the group consisting of HFO-1234yf, (E-/Z-)HFO-1234ze, and (E-/Z-)HFO-1225ye; and a chlorine-containing compound, wherein (1) the chlorine-containing compound is at least one member selected from the group consisting of $CH_2=CHCl$, $CHF=CHCl$, $CH_2=CFCl$, $CF_3Cl$, $CH_3Cl$, $CF_3CH_2Cl$, $CClF=CHCl$, and $CHF=CCl_2$, and (2) the chlorine-containing compound is contained in an amount ranging from 1 to 500000 mass ppm.

5 Claims, 2 Drawing Sheets

COMPOSITION CONTAINING HYDROFLUOROOLEFIN COMPOUND

TECHNICAL FIELD

The present invention relates to a composition comprising a hydrofluoroolefin (HFO) compound useful for applications, such as heat transfer media, foaming agents, solvents, cleaning agents, propellants, and fire extinguishers.

BACKGROUND ART

Hydrofluoroolefins (HFOs) represented by the formula: $CF_3(CX_2)_nCF=CH_2$, the formula: $CF_3(CX_2)_nCH=CHF$, and the like are useful compounds as, for example, various functional materials, solvents, refrigerants, foaming agents, monomers for functional polymers or starting materials of such monomers. For example, HFOs are used as monomers for modifying ethylene-tetrafluoroethylene copolymers.

Of the above HFO compounds, $CF_3CF=CH_2$ (HFO-1234yf), $CF_3CH=CHF$ (E-/Z-) (HF)-1234ze), and $CF_3CF=CHF$ (E-/Z-) (HFO-1225ye) have recently gained attention as they offer promising prospects as refrigerants with low global warming potential (GWP).

As an example of methods for producing the HFO compounds represented by the formulas above, a method has been reported in which a chlorine-containing alkane or chlorine-containing alkene starting material having the same number of carbon atoms as that of a target fluoroolefin is reacted with a fluorinating agent, such as an anhydrous hydrogen fluoride, in the presence of a catalyst (see, for example, Patent Literature (PTL) 1).

However, HFO compounds, which contain a double bond, have low stability, compared with hydrochlorofluorocarbons (HCFCs), hydrofluorocarbons (HFCs), and the like, which have been used as heat transfer media (refrigerants). Therefore, for example, an HFO compound when used as a heat transfer medium for an air-conditioning system may react with entrained air or oxygen, may react inside the air-conditioning system with a part or parts that are in contact with the heat transfer medium, or may result in decomposition of the HFO compound itself, depending on the operating conditions. In these cases, the performance of the air-conditioning system problematically decreases; thus, an improvement in the stability of the HFO compound is necessary.

Although the performance of air-conditioning systems has been improved in accordance with an improvement of the systems, there is a limit to improving the performance with the improvement of the systems, and an attempt has been made to improve, for example, the refrigerating capacity by adding an additive to an HFO compound used as a heat transfer medium.

CITATION LIST

Patent Literature

PTL 1: US2011/0160497

SUMMARY OF INVENTION

Technical Problem

An object of the present invention is to provide a composition comprising an HFO compound, the composition having excellent stability with decomposition and oxidation of the HFO compound being inhibited, the composition having improved refrigerating capacity when used as a heat transfer medium, compared with the case in which an HFO compound is used alone.

Another object of the present invention is to provide use of the composition having excellent stability in a heat transfer medium, a foaming agent, a solvent, a cleaning agent, a propellant, a fire extinguisher, or the like.

Solution to Problem

The present inventors conducted extensive research to achieve the above objects, and found that a composition comprising a specific HFO compound and a specific chlorine-containing compound can achieve the above objects. The present invention has thus been accomplished.

More specifically, the present invention relates to a composition comprising the following HFO compound.

1. A composition comprising: at least one HFO compound selected from the group consisting of HFO-1234yf, (E-/Z-) HFO-1234ze, and (E-/Z-)HFO-1225ye; and
a chlorine-containing compound,
wherein
(1) the chlorine-containing compound is at least one member selected from the group consisting of $CH_2=CHCl$, $CHF=CHCl$, $CH_2=CFCl$, $CF_3Cl$, $CH_3Cl$, $CF_3CH_2Cl$, $CClF=CHCl$, and $CHF=CCl_2$, and
(2) the chlorine-containing compound is contained in an amount ranging from 1 to 500000 mass ppm.

2. The composition according to Item 1, wherein the chlorine-containing compound is at least one member selected from $CH_2=CHCl$, $CHF=CHCl$, and $CH_2=CFCl$, and the chlorine-containing compound is contained in an amount of more than 6 mass ppm and 500000 mass ppm or less.

3. The composition according to Item 1, wherein the chlorine-containing compound is at least one member selected from $CH_2=CHCl$, $CHF=CHCl$, and $CH_2=CFCl$, and the chlorine-containing compound is contained in an amount of 10000 to 400000 mass ppm.

4. The composition according to Item 1, wherein the chlorine-containing compound is at least one member selected from $CH_2=CHCl$, $CHF=CHCl$, and $CH_2=CFCl$, and the chlorine-containing compound is contained in an amount of 100000 to 300000 mass ppm.

5. The composition according to any one of Items 1 to 4, wherein a mixture of the HFO compound and the chlorine-containing compound is an azeotrope or azeotrope-like mixture.

6. The composition according to any one of Items 1 to 4, wherein a mixture of the HFO compound and at least one chlorine-containing compound selected from $CH_2=CHCl$, $CHF=CHCl$, and $CH_2=CFCl$ is an azeotrope or azeotrope-like mixture.

7. The composition according to Item 1, wherein the chlorine-containing compound is at least one member selected from the group consisting of $CF_3Cl$, $CH_3Cl$, $CF_3CH_2Cl$, $CClF=CHCl$, and $CHF=CCl_2$, and the chlorine-containing compound is contained in an amount of 1 to 10000 mass ppm.

8. The composition according to any one of Items 1 to 7, further comprising at least one HFC compound selected from the group consisting of HFC-32, HFC-134a, HFC-125, HFC-143a, and HFC-23.

9. The composition according to any one of Items 1 to 8, further comprising at least one lubricant selected from the group consisting of polyalkylene glycols, esters, polyvinyl ethers, and alkylbenzenes.

10. The composition according to any one of Items 1 to 9, further comprising water, the water being contained in an amount of 1000 mass ppm or less.

11. The composition according to any one of Items 1 to 10, which is at least one member selected from the group consisting of heat transfer media, foaming agents, and propellants.

Advantageous Effects of Invention

The composition of the present invention, which comprises an HFO compound, comprises a specific HFO compound and a specific chlorine-containing compound, and the amount of the chlorine-containing compound is defined as ranging from 1 to 500000 mass ppm. Accordingly, the composition has excellent stability with decomposition and oxidation of the HFO compound being inhibited, and additionally, the refrigerating capacity when used as a heat transfer medium is improved, compared with the case in which an HFO compound is used alone. Therefore, the composition of the present invention is suitably used for applications, including heat transfer media, foaming agents, solvents, cleaning agents, propellants, fire extinguishers, and the like.

BRIEF DESCRIPTION OF DRAWINGS

In FIG. 1, R1140 refers to vinyl chloride.

In FIG. 2, R1140 refers to vinyl chloride.

DESCRIPTION OF EMBODIMENTS

Figure 1:
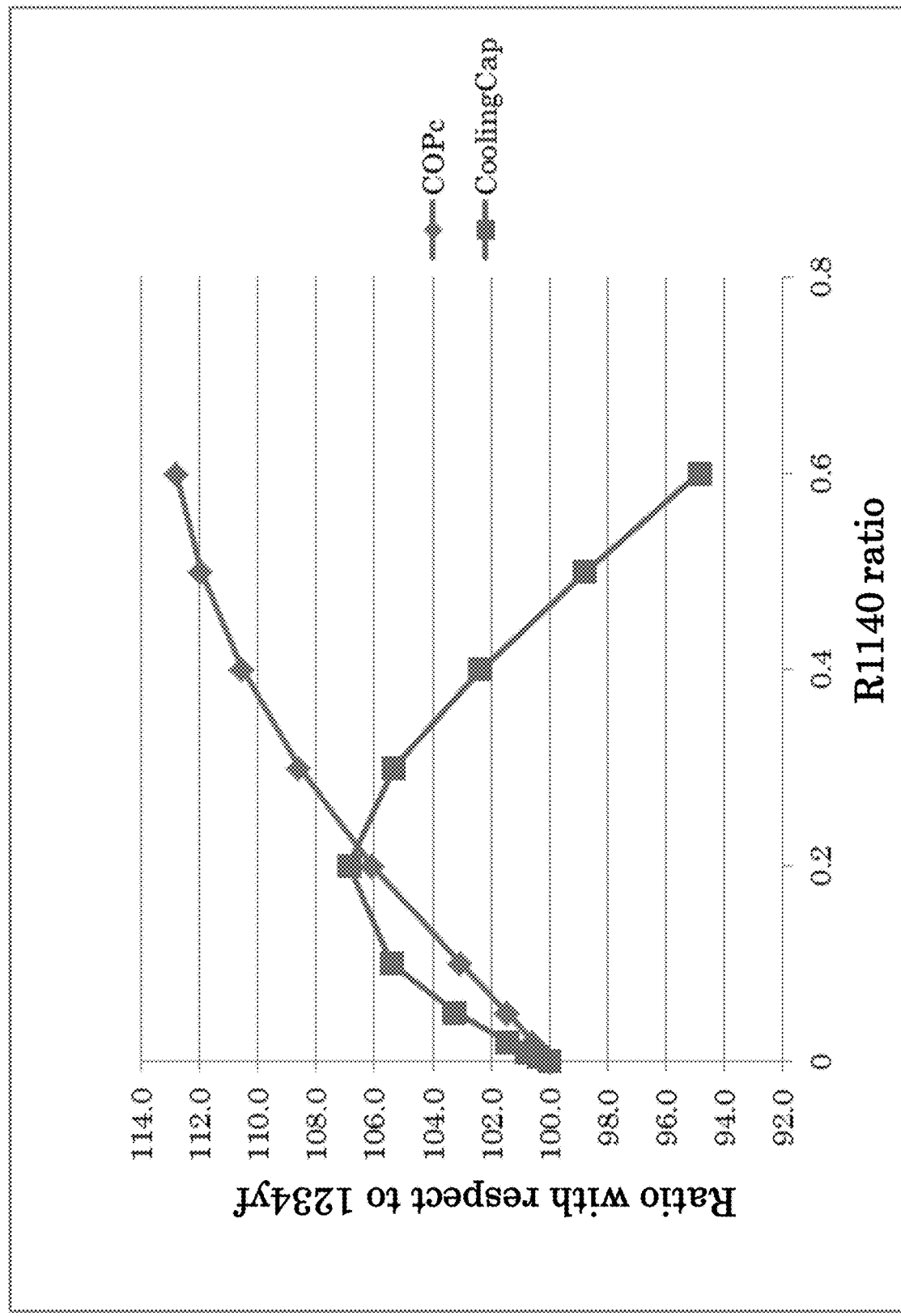
FIG. 1 is a graph showing the results of simulation evaluation performed with respect to the refrigerating capacity of a composition comprising a mixture of HFO-1234yf and $CH_2=CHCl$ (vinyl chloride) in a car air conditioner (Example 1).

The composition of the present invention, which comprises an HFO compound, is a composition comprising at least one HFO compound selected from the group consisting of HFO-1234yf, (E-/Z-)HFO-1234ze, and (E-/Z-)HFO-1225ye; and a chlorine-containing compound, wherein
(1) the chlorine-containing compound is at least one member selected from the group consisting of $CH_2=CHCl$, $CHF=CHCl$, $CH_2=CFCl$, $CF_3Cl$, $CH_3Cl$, $CF_3CH_2Cl$, $CClF=CHCl$, and $CHF=CCl_2$; and
(2) the chlorine-containing compound is contained in an amount ranging from 1 to 500000 mass ppm.
In this specification, the composition of the present invention, which comprises an HFO compound, also encompasses a mode of a composition that consists only of an HFO compound and a chlorine-containing compound. Further, in the present specification, the amount of the chlorine-containing compound refers to the amount in the entire composition.

The numerical range as used in this specification includes its lower limit and upper limit unless the term "less than" or "more than" is used. For example, the expression "1 to 500000 mass ppm" refers to 1 mass ppm or more and 500000 mass ppm or less.

The composition of the present invention, which has the above feature, comprises a specific HFO compound and a specific chlorine-containing compound, and the amount of the chlorine-containing compound is defined as ranging from 1 to 500000 mass ppm. Accordingly, the composition has excellent stability with decomposition and oxidation of the HFO compound being inhibited, and additionally, the refrigerating capacity when used as a heat transfer medium is improved, compared with the case in which an HFO compound is used alone. Therefore, the composition of the present invention is suitably used for applications, including heat transfer media, foaming agents, solvents, cleaning agents, propellants, fire extinguishers, and the like.

The composition of the present invention uses at least one HFO compound selected from the group consisting of HFO-1234yf, (E-/Z-)HFO-1234ze, and (E-/Z-)HFO-1225ye. Here, the "(E-/Z-)" indicates that one or both geometrical isomers, i.e., E- and Z-isomers, are included. Further, the term "HFO" refers to hydrofluoroolefin, and is distinguished from HFC (hydrofluorocarbon) or HCFC (hydrochlorofluorocarbon).

The above HFO compounds may be obtained by known production methods. Examples of the production methods include a method comprising subjecting fluoroalkane to a dehydrofluorination reaction in the presence of a catalyst (e.g., the method disclosed in JP2012-500182A).

More specifically, if the HFO compound is 2,3,3,3-tetrafluoropropene (HFO-1234yf), then 1,1,1,2,3-pentafluoropropane or 1,1,1,2,2-pentafluoropropane used as a starting material is subjected to a dehydrofluorination reaction in the presence of a catalyst to thus yield HFO-1234yf. If the HFO compound is 1,3,3,3-tetrafluoropropene ((E-/Z-)HFO-1234ze), then 1,1,1,3,3-pentafluoropropane used as a starting material is subjected to a dehydrofluorination reaction in the presence of a catalyst to thus yield (E-/Z-)HFO-1234ze. Further, if the HFO compound is 1,2,3,3,3-pentafluoropropene ((E-/Z-)HFO-1225ye), then 1,1,1,2,3,3-hexafluoropropane or 1,1,1,2,2,3-hexafluoropropane used as a starting material is subjected to hydrogenation, fluorination, and dehydrofluorination sequentially or simultaneously depending on the conditions, in the presence of a catalyst to thus yield (E-/Z-)HFO-1225ye.

In the above production methods, a chromium catalyst, such as chromium oxide or fluorinated chromium oxide, or other metal catalysts may be used as a catalyst. The reaction may be performed usually at a temperature within a range of 200 to 500° C. Additionally, the production of the HFO compound may be performed in accordance with known methods.

The composition of the present invention comprises at least one chlorine-containing compound selected from the group consisting of $CH_2=CHCl$ (vinyl chloride=R1140), $CHF=CHCl$ (HCFC-1131), $CH_2=CFCl$ (HCFC-1131a), $CF_3Cl$ (CFC-13), $CH_3Cl$ (methyl chloride), $CF_3CH_2Cl$ (HCFC-133a), $CClF=CHCl$ (HCFC-1121), and $CHF=CCl_2$ (HCFC-1121a) in an amount ranging from 1 to 500000 mass ppm. Of these, as a preferable mode, the composition of the present invention comprises at least one chlorine-containing compound selected from the group consisting of $CF_3Cl$ (CFC-13), $CH_3Cl$ (methyl chloride), $CF_3CH_2Cl$ (HCFC-133a), $CClF=CHCl$ (HCFC-1121), and $CHF=CCl_2$ (HCFC-1121a) in an amount ranging from 1 to 500000 mass ppm.

Incorporation of the above chlorine-containing compound allows the double bond in the molecule of the HFO compound to be present stably within the composition, thus inhibiting decomposition and oxidation of the HFO compound. This effect is presumably based on the fact that chlorine-containing compounds, which have higher reactivity than HFO compounds, react preferentially with air or oxygen, inhibiting decomposition and oxidation of the HFO compounds.

Incorporation of the above chlorine-containing compound also improves the refrigerating capacity when used as a heat transfer medium, compared with the case in which an HFO compound is used alone.

The above chlorine-containing compounds may together form oligomers, such as dimers to decamers. Further, the chlorine-containing compound may form such oligomers with a portion of the HFO compound. In these cases, if used as a heat transfer medium, the composition can also improve the slidability within a refrigerator, leading to an improvement of the performance of the refrigerator.

As in $CH_2=CHCl$ (vinyl chloride), some of the above chlorine-containing compounds have a characteristic odor (e.g., $CH_2=CHCl$ has a chloroform odor). Thus, if a chlorine-containing compound with an odor is used, it is also possible to achieve the function of a tracer for detecting the leakage of the composition.

The chlorine-containing compound may be externally added to the HFO compound. The chlorine-containing compound may also be a compound that is obtained as a by-product in the course of the production process of the HFO compound. If the latter is the case, the amount of the chlorine-containing compound is adjusted to be within a range of 1 to 500000 mass ppm by adjusting the amount of the by-product.

The amount of the chlorine-containing compound in the composition is within a range of 1 to 500000 mass ppm, preferably about 10000 to 400000 mass ppm, and more preferably about 100000 to 300000 mass ppm.

If the chlorine-containing compound is at least one member selected from $CH_2=CHCl$, $CHF=CHCl$ and $CH_2=CFCl$, the amount of the chlorine-containing compound is preferably more than 6 mass ppm and 500000 mass ppm or less, more preferably about 10000 to 400000 mass ppm, and most preferably about 100000 to 300000 mass ppm.

If the chlorine-containing compound is at least one member selected from the group consisting of $CF_3Cl$, $CH_3Cl$, $CF_3CH_2Cl$, $CClF=CHCl$, and $CHF=CCl_2$, the amount of the chlorine-containing compound is preferably about 1 to 10000 mass ppm.

Of these chlorine-containing compounds, it is preferable to select a chlorine-containing compound that foils an azeotrope or azeotrope-like mixture with the HFO compound. For example, at least one member of $CH_2=CHCl$, $CHF=CHCl$, and $CH_2=CFCl$ is suitably used. The use of a combination that forms an azeotrope or azeotrope-like mixture lowers the boiling point, compared with the use of a combination that forms a non-azeotropic mixture, leading to an improvement in the refrigerating capacity when used as a heat transfer medium.

In addition to the HFO compound and chlorine-containing compound, the composition of the present invention may comprise an HFC compound, an HCFC compound, $CO_2$, and the like, which are known as existing heat transfer media. Examples include HFC-32, HFC-134a, HFC-125, HFC-143a, HFC-23, and the like. These additives may be used together so as to adjust the refrigerating capacity, GWP, flammability, and the like of the composition of the present invention, to an extent that the effects of the present invention are not hindered. The amount of these additives is preferably, but is not limited to, 40 mass % or less, per 100 mass % of the total amount of the HFO compound and these additives.

For use as a heat transfer medium, the composition of the present invention may further comprise at least one lubricant selected from the group consisting of polyalkylene glycols, esters, polyvinyl ethers, and alkylbenzenes. The lubricant can be incorporated in an amount of 10 to 50 mass % into the composition. However, the amount is not limited to this range, and can vary depending on the specification of the oil tank of a refrigerator. If the amount is within this range, it is unlikely that the stability of the HFO compound will be impaired.

The composition of the present invention may further comprise water. The amount of water is preferably 1000 mass ppm or less, and more preferably 200 mass ppm or less. When water is contained in an amount within a range of 1000 mass ppm or less, the stability of the HFO compound further improves, compared with the case where water is not contained.

The type of water is not particularly limited, and purified water, such as distilled water, ion exchange water, filtered water, tap water, and ultrapure water obtained by a commercially available device for generating pure water, etc., can be used. Water may possibly be mixed in the process of producing the HFO compound, and the water mixed at this time may be used as water to be incorporated into the composition. As a matter of course, it is possible to once remove the water generated in the production process, and use separately prepared water as water to be incorporated into the composition. The pH of the water is not particularly limited, and is usually within a range of 6 to 8.

EXAMPLES

The present invention is described in more detail below with reference to Examples. However, the present invention is not limited to the embodiments in the Examples.

Example 1

A simulation evaluation was performed with respect to the refrigerating capacity of a composition comprising a mixture of HFO-1234yf and $CH_2=CHCl$ (vinyl chloride=R1140) in a car air conditioner. FIG. 1 shows the results.

FIG. 1 reveals that the coefficient of performance (COP) improves with the addition of vinyl chloride even when it is a small amount added, compared with when HFO-1234yf is used alone. FIG. 1 also reveals that the refrigerating capacity is more excellent when the composition ratio of vinyl chloride is within a range of more than 0 to 0.55 or less, compared with when HFO-1234yf is used alone, and that the refrigerating capacity is maximal when the vinyl chloride composition ratio is about 0.2.

Example 2

Figure 2:
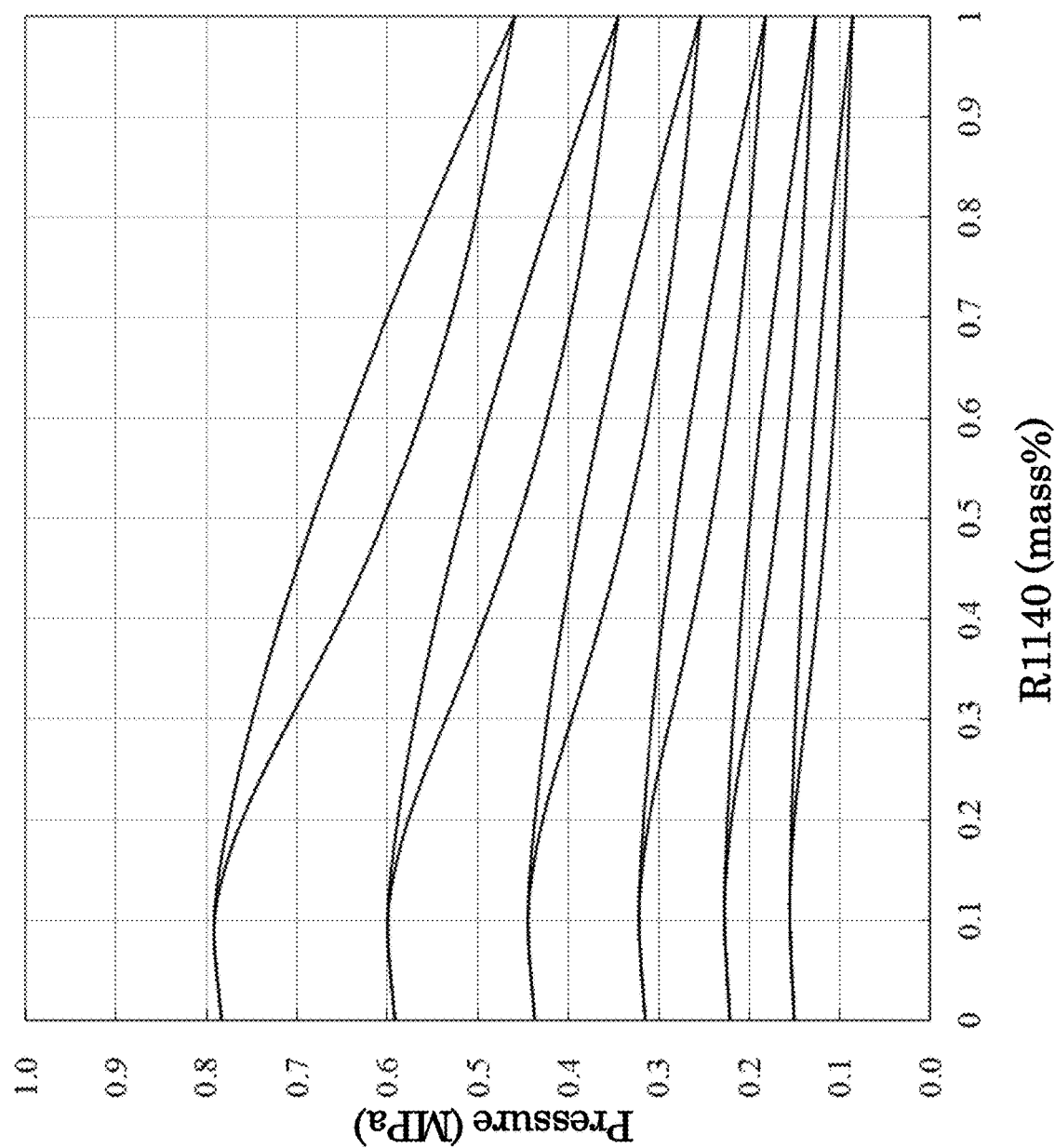
FIG. 2 is a graph showing the measurement results of the vapor-liquid equilibrium of a composition comprising a mixture of HFO-1234yf and $CH_2=CHCl$ (vinyl chloride) (Example 2).

The vapor-liquid equilibrium of a composition comprising a mixture of HFO-1234yf and $CH_2=CHCl$ (vinyl chloride=R1140) was measured. FIG. 2 shows the results.

FIG. 2 reveals that when the composition ratio of HFO-1234yf:vinyl chloride is 1:0 to 0.8:0.2, the composition is an azeotropic composition or azeotrope-like composition.

The results of FIGS. 1 and 2 reveal that the composition comprising a mixture of HFO-1234yf and vinyl chloride has an excellent refrigerating capacity at a composition ratio within a range of more than 0 to 0.55 or less, and that it is more preferable when the composition ratio of vinyl chloride is within a range of 0.1 to 0.3.

The invention claimed is:

1. A heat transfer media comprising:
   at least one HFO compound selected from the group consisting of 2,3,3,3-tetrafluoropropene (HFO-1234yf), (trans-/cis-)1,3,3,3-tetrafluoropropene ((E-/Z-)HFO-1234ze), and (trans-/cis-)1,2,3,3,3-pentafluoropropene ((E-/Z-)HFO-1225ye);
   a chlorine-containing compound; and
   at least one HFC compound selected from the group consisting of difluoromethane (HFC-32), 1,2,2,2-tetrafluorothane (HFC-134a), 1,1,1,2,2-pentafluoroethane (HFC-125), 1,1,1-trifluoroethane (HFC-143a), and trifluoromethane (HFC-23),
   wherein
   (1) the chlorine-containing compound is at least one member selected from the group consisting of $CH_2=CHCl$ and $CH_2=CFCl$, and
   (2) an amount of the chlorine-containing compound A in the heat transfer media is within a range of 1 to 400000 mass ppm.

2. The heat transfer media according to claim 1, wherein the amount of the chlorine-containing compound in the heat media transfer is within a range of 100000 to 300000 mass ppm.

3. The heat transfer media according to claim 1, wherein a mixture of the HFO compound and the chlorine-containing compound is an azeotrope or azeotrope-like mixture.

4. The heat transfer media according to claim 1, further comprising at least one lubricant selected from the group consisting of polyalkylene glycols, polyvinyl ethers, and alkylbenzenes.

5. The heat transfer media according to claim 1, further comprising water, the water being contained in an amount of 1000 mass ppm or less.

* * * * *